(12) United States Patent
Hiejima

(10) Patent No.: US 6,554,805 B2
(45) Date of Patent: Apr. 29, 2003

(54) INFUSION RATE ADJUSTING DEVICE FOR DRUG SOLUTION INJECTOR

(75) Inventor: Katsuhiro Hiejima, Osaka (JP)

(73) Assignee: Nipro Corp., Osaka (JP)

( * ) Notice: Subject to any disclaimer, the term of this patent is extended or adjusted under 35 U.S.C. 154(b) by 0 days.

(21) Appl. No.: 09/794,136

(22) Filed: Feb. 28, 2001

(65) Prior Publication Data

US 2001/0021829 A1 Sep. 13, 2001

(30) Foreign Application Priority Data

Feb. 29, 2000 (JP) .................................. 2000-053236

(51) Int. Cl.[7] .............................................. A61M 5/00
(52) U.S. Cl. ........................ 604/247; 604/30; 604/246
(58) Field of Search ................................ 604/246, 247, 604/153, 276, 257, 30; 137/511, 512

(56) References Cited

U.S. PATENT DOCUMENTS

| | | | |
|---|---|---|---|
| 3,941,149 A | | 3/1976 | Mittleman |
| 4,246,932 A | * | 1/1981 | Raines ........................ 137/512 |
| 4,729,401 A | * | 3/1988 | Raines ........................ 604/246 |
| 4,756,982 A | | 7/1988 | McCartney, Jr. et al. |
| 4,919,167 A | * | 4/1990 | Manska ........................ 604/247 |
| 5,310,094 A | | 5/1994 | Martinez et al. |
| 5,697,904 A | * | 12/1997 | Raines et al. ................ 604/247 |

FOREIGN PATENT DOCUMENTS

| | | |
|---|---|---|
| DE | 295 19 322 | 3/1996 |
| EP | 0 947 752 A1 | 10/1999 |
| JP | A9280394 | 10/1997 |
| JP | A1028741 | 2/1998 |
| JP | a10113386 | 5/1998 |

* cited by examiner

Primary Examiner—Steven J. Ganey
(74) Attorney, Agent, or Firm—Birch, Stewart, Kolasch & Birch, LLP

(57) ABSTRACT

An infusion rate adjusting device for drug solution injectors comprises a tubular flow control unit including plural check valves of different opening pressures, and means for selecting one of said check valves to adjust an infusion rate of the drug solution. The infusion rate adjusting device is simple in operation to set out an infusion rate of the drug solution and is considerably reduced in the production cost.

5 Claims, 4 Drawing Sheets

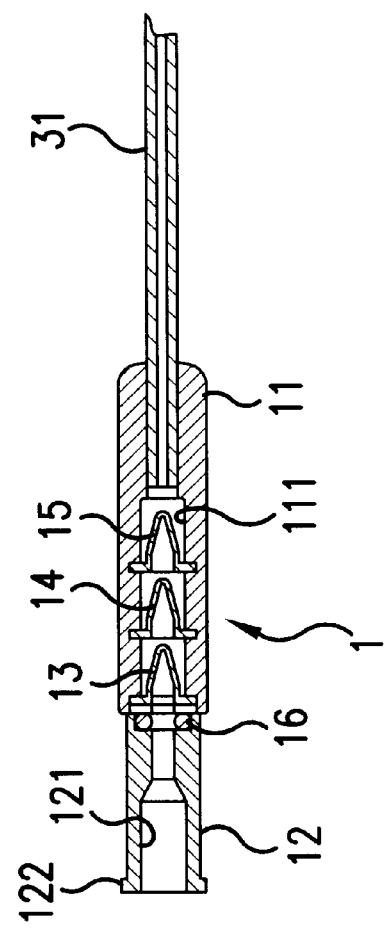
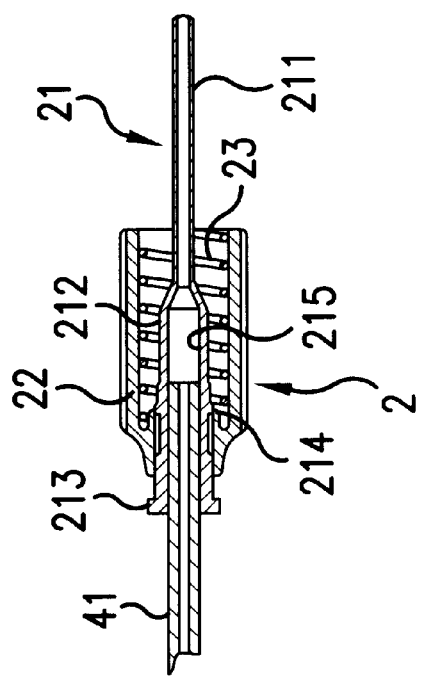
FIG.1

INFUSION RATE ADJUSTING DEVICE FOR DRUG SOLUTION INJECTOR

FIELD OF THE INVENTION

The present invention relates to an infusion rate adjusting device for drug solution injectors used for injecting a very small quantity of a drug solution such as, for example, an anesthetic agent, or an analgetic agent or antibiotic agent contained in a reservoir, into a patient's body under the action of an external force such as a contractile force of elastic materials with rubberlike elasticity, expansion force of springs, or a pushing force due to a negative pressure chamber.

BACKGROUND OF THE INVENTION

The drug solution injectors have been used for injecting a very small amount of a drug solution contained in a vial into a patient's body by applying a contractile force of an elastic material having rubber-like elasticity on a reservoir for drug solution. In such injectors of the prior art, a fine tube has been used to infuse the drug solution into the body and the infusion rate of the drug solution is adjusted by a resistance of passage which varies with an internal diameter and length of the fine tube. This makes it possible to adjust the infusion rate to a desired value by adjustment of the internal diameter or length of the fine tube. For this reason, the drug solution injectors are marketed in combination of one fine tube per a reservoir.

In recent years, however, some cases need to change the infusion rate during infusion of the drug solution according to changes of the patient's condition. In order to change the infusion rate during infusion of the drug soluiton, some flow rate control devices have been proposed in Japanese patent applications by Nissho Corporation. For example, JP-A-H9-280394 and JP-A-H10-28741 disclose a flow rate control device of the kind wherein plural fine tubes of different resistances of passages are respectively connected to a valve, and the flow rate of the drug solution is adjusted by changing over the valve. JP-A-H10-113386 discloses a flow rate control device of the kind wherein plural fine tubes are arranged in parallel and the flow rate of the drug solution is adjusted by opening or closing the fine tube with a clamp.

However, the above flow rate control devices have complex passages for the drug solution and are relatively difficult to operate setting of the inflow rate for the fine tube. On the other hand, the drug injectors of the kind wherein the force applied to the reservoir is reduced by the resistance of passage in the fine tube makes it possible to perform relatively fine adjustment at the accuracy of ±10%. However, the accuracy of the infusion rate is affected by tolerance of the internal diameter of the fine tube. Thus, the drug injectors using fine tubes of high precision result in high manufacturing cost.

In view of the above circumstances, the present invention has been made for the purpose of providing an infusion rate adjusting device for drug solution injectors, which is simple in operation to set out an infusion rate of the drug solution and which is considerably reduced in the manufacturing cost.

SUMMARY OF INVENTION

The present invention has been achieved on the basis of the idea that the above object is be achieved by arranging plural check valves of different opening pressures in a passage of a drug solution in series or in parallel so that the operator can select one of the check valves corresponding to a desired flow rate of the drug solution during infusion.

According to the present invention, there is provided an infusion rate adjusting device for drug solution injectors, which comprises a tubular flow control unit including plural check valves of different opening pressures, and means for selecting one of said check valves to adjust an infusion rate of the drug solution. In one preferred embodiment, the flow control unit includes plural check valves of a duck bill type, which are arranged in series and in descending order of opening pressures from the upstream side to the downstream side. In this case, it is preferred to use check valve selecting means including a tubular rod capable of being inserted into said check valve through a lumen of the flow control unit from the upstream side thereof to adjust the injection rate of the drug solution. The infusion rate of the drug solution is determined by the check valve which is not yet opened by the rod and is present in the upstream side of the lumen.

Preferably, the check valve selecting means including the rod is provided with a female engaging member having female engaging means and rotatably fitted on the rod, said female engaging means is adapted to be engaged with the male engaging means provided on the proximal end of the flow control unit so that the rod is linearly moved within the lumen of the flow control unit by rotating the female engaging member.

In another preferred embodiment, the flow control unit includes plural check valves of an umbrella type having different opening pressures arranged in series within a lumen of the tubular member. In this case, each of the check valves has a drug passage formed on its axis and, when the drug passage of one of the check valves is closed by said check valve selecting means, the check valve with the closed drug passage serves as the check valve which determines the injection rate. Preferably, such check valve selecting means serving as the passage closing means is provided the sidewall of the flow control unit.

BRIEF DESCRIPTION OF THE DRAWING

The present invention will become more fully understood from the detailed description given below and the accompanying drawings which are given by way of illustration only, and thus are not limitative of the present invention, and wherein:

FIG. 1 is a cross sectional view of one embodiment of an infusion rate-adjusting device of the present invention;

DETAILED DESCRIPTION OF THE INVENTION

Figure 2:
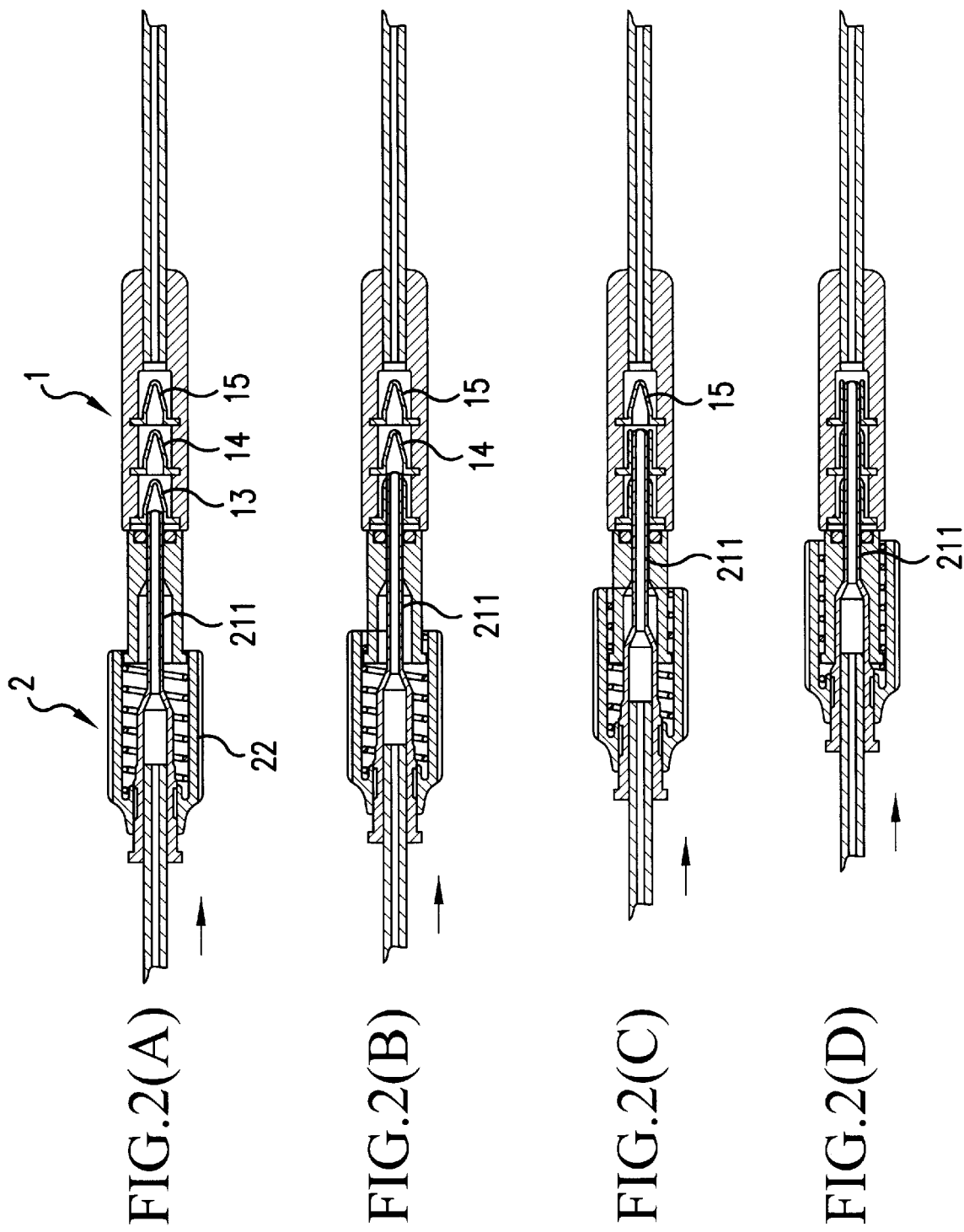
FIG. 2 is a schematic diagram illustrating the operation of the infusion rate-adjusting device of FIG. 1.

The present invention is hereinafter described with reference to the accompanying drawings that illustrate some examples of an infusion rate-adjusting device according to the present invention. It is to be understood that no limitation to the scope of the claims which follow is intended by the following description. Those skilled in the art will recognize that these infusion rate-adjusting device presented in the drawings may be modified in many aspects without departing from the basic overall concept of the invention.

Figure 3:
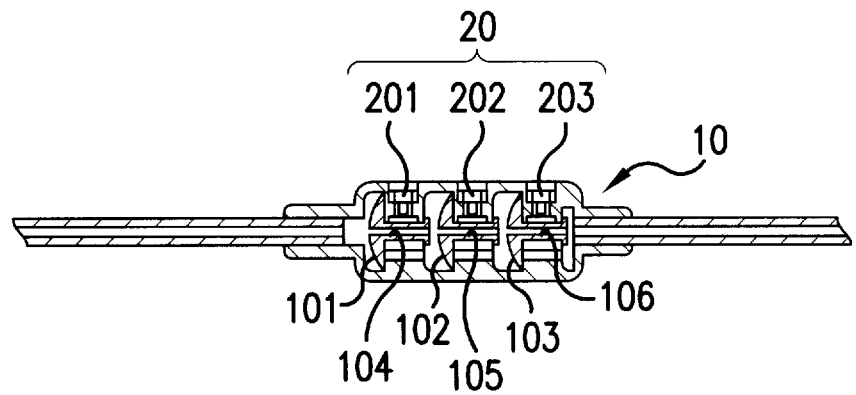
FIG. 3 is a cross sectional view of another embodiment of an infusion rate-adjusting device of the present invention.

As illustrated in FIG. 1 and FIG. 3, each infusion rate adjusting device of the present invention generally comprises a tubular flow control unit 1, 10 provided with plural check valves of different opening pressures, and a check valve selecting means or unit 2, 20 for selecting one of the check valves that determines an infusion rate of the drug solution.

Referring now to FIG. 1, there is shown one embodiment of the infusion rate adjusting device of the present invention, which comprises a flow control unit 1 provided with plural numbers of check valves 13, 14, 15 of a duck bill type, said check valves 13, 14, 15 being arranged in series and in descending order of the opening pressures from an upstream side to a downstream side; and a check valve selecting means unit 2 including a tubular rod 21 capable of being passed through the check valves 13, 14, 15 to select one check valve 13 or 14 or 15 that determines a infusion rate. The infusion rate is determined by the check valve 13 or 14 or 15 that has not been penetrated by the rod 21 and located in the uppermost streamside of the passage.

The flow control unit 1 includes a tubular body composed of a distal member 11 and a proximal member 12. The distal member 11 has with a stepped lumen and is provided with plural numbers of check valves 13, 14, 15 of a duck bill type having different opening pressures. The check valves 13, 14, 15 are arranged within a large-sized lumen 111 of the distal member 11 in series and in the descending order of the opening pressures from an upstream side (i.e., a proximal side) to a downstream side (a distal side) of the lumen or passage of the distal member 11. The distal member 11 is provided at the distal end thereof with a connecting tube 31 that is to be connected to a connector 3, by fitting its one end in a small-sized lumen.

The proximal member 12 has a lumen 121 formed into a complementary configuration with respect to an engaging portion 22 of the rod 21 of the check valve selecting means 2. The proximal member 12 is provided at the proximal end thereof with a male engaging means or external thread 122 to fix the check valve selecting means 2 to the flow control unit 1 by engagement with a female engaging member 22 of the check valve selecting means 2 as mentioned below. The proximal member 12 is provided at the distal end thereof with an O-ring 16 to form a liquid-tight seal between the lumen 121 of the proximal member 12 and an outer wall of the rod 21 inserted therein. The O-ring 16 is located at a position close to the check valve 13 of the uppermost stream side that has the largest opening pressure, when the proximal member 12 is incorporated into the flow control unit 1.

Figure 5:
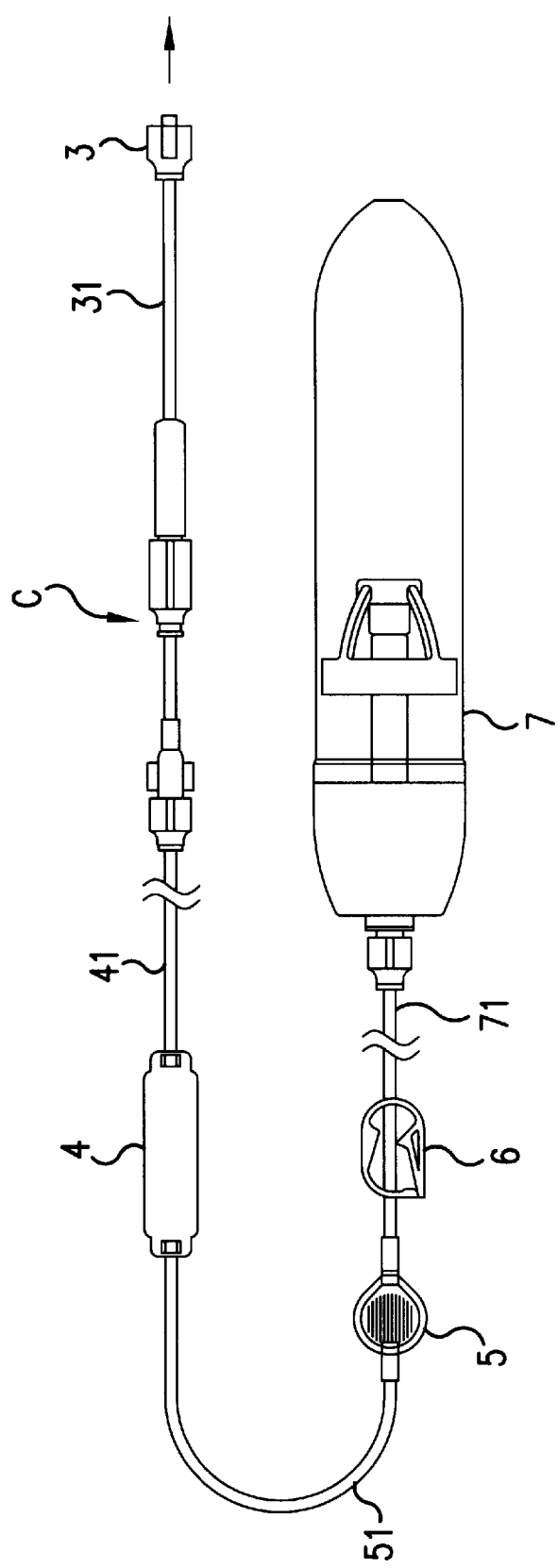
FIG. 5 is a schematic diagram illustrating an example of a drug solution injector with the infusion rate-adjusting device of FIG. 1.

The check valve selecting means 2 has a distal end and a proximal end and is composed of a tubular rod 21 capable of being passed through the check valves 13, 14, 15; and a female engaging member 22 having female engaging means or internal thread 23 and rotatably fitted on the rod 21 at the proximal end thereof. The check valve selecting means 2 is connected at the proximal end thereof to a connecting tube 41 by inserting one end thereof into the lumen of the rod 21. The other end of the connecting tube 41 is connected to the flow control device 4 illustrated in FIG. 5. The drug solution flowing out of the flow control device 4 flows into the lumen 215 of the rod 21 through the connecting tube 41. The rod 21 is a slender hollow member composed of a relatively small-diameter portion 211 to be inserted into the flow control unit 1, and a relatively large-diameter portion 212 on which the female engaging member 22 is rotatably fitted. The female engaging member 22 is a hollow cylindrical member provided with an internal thread serving as the female engaging means 23. The female engaging member 22 is rotatable around the rod 21 and movable between an annular flange 213 provided on the proximal end of the rod 21 and an annular rib 214 provided on the relatively large-diameter portion 212 of the rod 21 at a position spaced from the annular flange 213 toward the distal side of the rod 21.

The infusion rate adjusting device C is located at the downstream side from the flow rate control device 4 and adjusts the flow rate of the drug solution which had been discharged from the reservoir 7 and controlled by the flow control device 4 to the desired flow rate. In the drawings, numeral 3 is a connector, 31, 41, 51 and 71 each indicates a connecting tube, 5 indicates a filter and 6 is a clamp.

In use, the infusion rate is adjusted by the infusion rate-adjusting device C of FIG. 1 in the following manner mentioned hereinafter with reference to FIG. 2.

In FIG. 2, (A) illustrates the infusion rate adjusting device C under the condition where none of the check valves 13, 14 and 15 is penetrated by the rod 21 of the check valve selecting means 2. Thus, the infusion rate is determined by the check valve 13 with the highest opening pressure, which is located at the uppermost stream of the lumen of the flow control unit 1.

(B) illustrates the infusion rate-adjusting device C under the condition where only the check valve 13 has been penetrated by the rod 21 of the check valve selecting means 2. Thus, the infusion rate is determined or adjusted by the check valve 14 with the middle opening pressure.

(C) illustrates the infusion rate adjusting device C under the condition where the check valves 13 and 14 have been penetrated by the rod 21 of the check valve selecting means 2. Thus, the infusion rate is determined or adjusted by the lowermost stream check valve 15.

(D) illustrates the infusion rate adjusting device C under the condition where all the check valves 13, 14 and 15 have been penetrated by the rod 21 of the check valve selecting means 2. Thus, adjustment of the infusion rate is never carried out.

Referring now to FIG. 3, there is illustrated another embodiment of the present invention, which will be explained below with reference to FIGS. 3 and 4.

As illustrated in FIG. 3, the flow control unit 10 is provided with plural check valves 102, 103 and 104 of an umbrella type having an opening pressure different from one another and arranged in series in the order of decreasing opening pressures. Each of the check valves 101, 102 and 103 has a drug passage 104, 105, 106 on the axis thereof. In this case, passage-blocking means 201, 202, 203 for blocking the drug passage 104, 105, 106 of the check valves 101, 102, 103 are used as the check valve selecting means 20. When one of the drug passages 104, 105 and 106 of the check valves 101, 102 and 103 is blocked by the check valve selecting means 20, the check valve 101, 102 or 103 with the blocked drug passage 104, 105 or 106 serves as the check valve.

Using the infusion rate-adjusting device of FIG. 3, the infusion rate is adjusted in the following manner mentioned below with reference to FIG. 4.

Figure 4A:
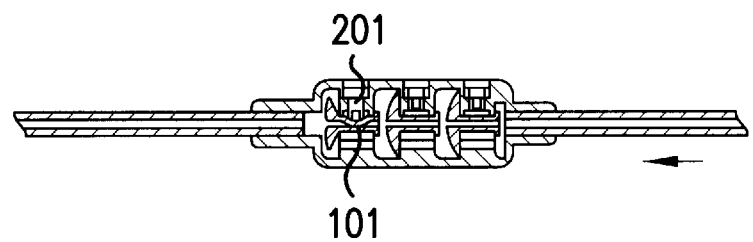
FIG. 4 is a schematic diagram illustrating the operation of the infusion rate-adjusting device of FIG. 3.
Figure 4B:
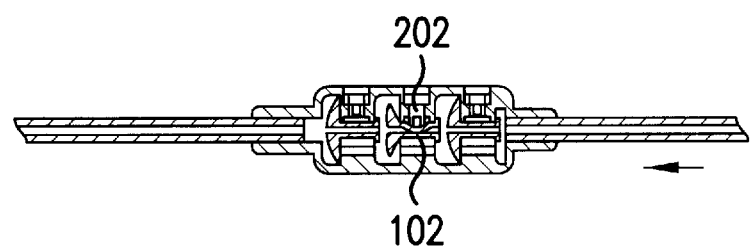
Figure 4C:
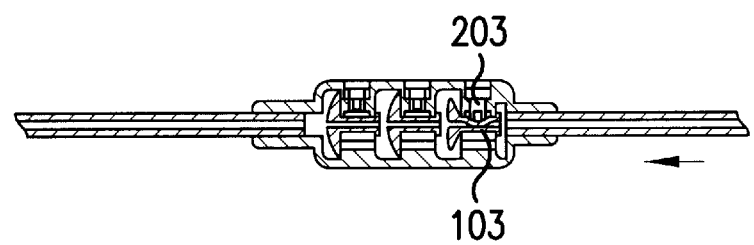

In FIG. 4, (A) illustrates the infusion rate-adjusting device under the condition where the drug passage 104 of the check valve 101 is blocked by the passage-blocking means 201. In this case, the infusion rate is determined or adjusted by the opening pressure of the check valve 101.

(B) illustrates the infusion rate-adjusting device under the condition where the drug passage 105 of the check valve 102 is blocked by the passage-blocking means 202. In this case, the infusion rate is determined or adjusted by the opening pressure of the check valve 102.

(C) illustrates the infusion rate-adjusting device under the condition where the drug passage 106 of the check valve 103 is blocked by the passage-blocking means 203. In this case, the infusion rate is determined or adjusted by the opening pressure of the check valve 103.

EXAMPLES 1 and 2

There were prepared infusion rate adjusting devices each having a structure shown in FIG. 1 and including check valves 13, 14 and 15 with opening pressures of 2.5 kPa, 5 kPa, 10 kPa respectively. Also, there were prepared infusion rate adjusting devices each having a structure shown in FIG. 1 and including check valves 13, 14 and 15 with opening pressures of 12.5 kPa, 25 kPa, 30 kPa respectively.

For each of the above infusion rate-adjusting device, the reduction in flow rate was determined under the condition in which a compression pressure of the reservoir is set to 60 kPa. The results are shown in Table 1. From the results, about 4.2% reduction in flow rate per 2.5 kPa of the opening pressure of valve is recognized.

Example 1

| | Opening pressure of valve | reduction in flow rate |
|---|---|---|
| valve 13 | 10 kPa | 16% |
| valve 14 | 5 kPa | 8.3% |
| valve 15 | 2.5 kPa | 4.2% |

Example 2

| Opening pressure of valve | reduction in flow rate |
|---|---|
| 30 kPa | 50% |
| 25 kPa | 43% |
| 12.5 kPa | 21% |

As will be understood from the above explanation, the present invention makes it easy to perform operation for setting the infusion rate of the drug solution injectors by use of the infusion rate adjusting device of the present invention. In addition, the present invention makes it possible to provide the infusion rate-adjusting device for drug solution injectors with ease.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An infusion rate adjusting device for drug solution injectors used for injecting a drug solution, comprising a tubular flow control unit including plural check valves of different opening pressures, and means for selecting one of said check valves to adjust an infusion rate of the drug solution.

2. The infusion rate adjusting device according to claim 1, wherein said flow control unit is provided with plural check valves of an umbrella type having different opening pressures and being arranged in series within a lumen of the tubular member, each of said check valves having a drug passage formed on its axis, and wherein when the drug passage of one of the check valves is closed by said check valve selecting means, the check valve with the closed drug passage serves as the check valve which determines the injection rate.

3. The infusion rate adjusting device according to claim 2, wherein said check valve selecting means is passage-closing means provided in the side wall of the flow control unit.

4. An infusion rate adjusting device for drug solution injectors used for injecting a drug solution, comprising a tubular flow control unit including plural check valves of different opening pressures, and means for selecting one of said check valves to adjust an infusion rate of the drug solution, wherein said tubular flow control unit includes plural check valves of a duck bill type, said check valves being arranged in series and in descending order of opening pressures from the upstream side to the downstream side, and wherein said check valve selecting means includes a tubular rod capable of being inserted into said check valve through a lumen of the flow control unit from an upstream side thereof to adjust the injection rate of the drug solution, the injection rate of the drug solution being determined by the check valve which is not yet opened by the rod and is present in the most upstream side of the lumen.

5. The infusion rate adjusting device according to claim 4, wherein said check valve selecting means includes a female engaging member provided with female engaging means and rotatably fitted on the rod at the proximal end thereof, said female engaging means being engaged with male engaging means provided on the proximal end of the flow control unit so that the rod is linearly moved within the lumen of the flow control unit by rotating the female engaging member.

* * * * *

UNITED STATES PATENT AND TRADEMARK OFFICE
CERTIFICATE OF CORRECTION

PATENT NO. : 6,554,805 B2
DATED : April 29, 2003
INVENTOR(S) : Katsuhiro Hiejima It is certified that error appears in the above-identified patent and that said Letters Patent is hereby corrected as shown below:

<u>Title page,</u>
Item [73], "Nipro Corp." should read as -- Nipro Corporation --.

Signed and Sealed this

Twelfth Day of August, 2003

JAMES E. ROGAN
*Director of the United States Patent and Trademark Office*